United States Patent [19]
Weber et al.

[11] Patent Number: 5,145,488
[45] Date of Patent: Sep. 8, 1992

[54] PROCESS FOR THE PREPARATION OF MIXTURES OF OIL-SOLUBLE IRON AND MAGNESIUM SALTS OF SATURATED ALIPHATIC MONOCARBOXYLIC ACIDS AND THEIR USE

[75] Inventors: Jürgen Weber, Oberhausen; Peter Lappe; Werner De Win, both of Dinslaken; Wolfgang Nierhaus, Moers, all of Fed. Rep. of Germany

[73] Assignee: Hoechst Aktiengesellschaft, Fed. Rep. of Germany

[21] Appl. No.: 589,375

[22] Filed: Sep. 27, 1990

[30] Foreign Application Priority Data

Sep. 28, 1989 [DE] Fed. Rep. of Germany ....... 3932322

[51] Int. Cl.$^5$ ............................................. C10L 10/00
[52] U.S. Cl. ....................................... 44/363; 44/385; 44/457; 252/36
[58] Field of Search ......................... 44/363, 385, 457; 252/36

[56] References Cited

U.S. PATENT DOCUMENTS

| 2,844,112 | 7/1958 | Muller | 44/363 |
| 3,231,592 | 1/1966 | McCord | 260/414 |
| 3,446,749 | 5/1969 | Weisfeld et al. | 252/400 |
| 3,501,279 | 3/1970 | Allen et al. | 44/70 |
| 4,994,090 | 2/1991 | Rodriguez | 44/457 |

FOREIGN PATENT DOCUMENTS

| 58330 | 8/1982 | European Pat. Off. |
| 0188115 | 7/1986 | European Pat. Off. |
| 3044907 | 6/1982 | Fed. Rep. of Germany |
| 3729930 | 3/1989 | Fed. Rep. of Germany |

*Primary Examiner*—Prince Willis, Jr.
*Assistant Examiner*—Thomas Steinberg
*Attorney, Agent, or Firm*—Jordan B. Bierman

[57] ABSTRACT

To prepare a mixture of oil-soluble iron and magnesium salts of saturated aliphatic $C_6$ to $C_8$ monocarboxylic acids, magnesium oxide is reacted with a $C_6$ to $C_8$ monocarboxylic acid in a solution of an iron salt of a saturated $C_6$ to $C_8$ monocarboxylic acid. The mixture is used as a combustion auxiliary.

16 Claims, No Drawings

PROCESS FOR THE PREPARATION OF MIXTURES OF OIL-SOLUBLE IRON AND MAGNESIUM SALTS OF SATURATED ALIPHATIC MONOCARBOXYLIC ACIDS AND THEIR USE

This Application claims the priority of German Application P 39 32 322.6, filed Sep. 28, 1989.

The invention relates to a process for the preparation of mixtures of iron salts and magnesium salts of saturated aliphatic monocarboxylic acids having 6 to 8 carbon atoms and the use of these mixtures as combustion auxiliaries for liquid fuels.

BACKGROUND OF THE INVENTION

The more efficient use of petroleum made necessary by the shortage and increased costs thereof have led, inter alia, to the development of processes which guarantee the optimum possible utilization of this raw material. A considerable proportion of petroleum is converted into heavy and light heating oil and used for generating energy, in particular for producing heat and electricity. The efficiency which can be achieved depends on the completeness of the combustion of the fuel. Various measures which effect complete combustion, i.e. avoid the formation of carbon black, are therefore employed.

One way of achieving this aim is to add certain substances to the heating oil which promote its combustion. Sulfonates and naphthenates of various metals have been known for a long time as additives which suppress the formation of carbon black (cf, for example, J. Vaerman, Journal of the Institute of Petroleum, Volume 50, No. 487 (1964), pages 155–168). Suspended inorganic metal salts and metal oxides also have a marked combustion-promoting effect (cf P. J. Agius et al., 8th World Petroleum Congress Proceedings 5, 27–33 (1971) but, like metal chelates, acetylacetonates, and ferrocene, they have the disadvantage that they readily separate out from the suspension.

Iron and manganese salts of aliphatic carboxylic acids having 10 to 30 carbon atoms are known (from French Patent 1,381,150) as additives which improve the combustion of liquid fuels. Finally, the use of iron salts and/or manganese salts of aliphatic carboxylic acids having 6 to 8 carbon atoms as combustion auxiliaries is described in DE 30 44,907 C2. These compounds have the advantage of being easily oil-soluble and non-toxic, and moreover readily available.

The formation of carbon black is indeed suppressed completely or almost completely during combustion of liquid fuels by using the above-mentioned additives. However, these contribute nothing towards solving the sulfur problem. Both heavy and light heating oils contain greater or lesser proportions of bonded sulfur, depending on their origin. This sulfur is partly burned in the flame to form $SO_3$, vanadium compounds inter alia likewise contained in the heating oils acting as catalysts. Moreover, $SO_3$ forms corrosive sulfuric acid in the presence of water. To avoid damage to the combustion equipment, the waste gases must therefore be heated above the dew point of the acid in order to prevent condensation of the acid.

Although major damage from corrosion can be excluded by construction measures, because of the diversity of consumers with their different furnaces, a different route is taken in practice. It has been found that the formation of sulfuric acid can be avoided by addition of magnesium in the form of a compound which is dissolved in the heating oils. The magnesium oxide formed during combustion of the magnesium compound deactivates the substances which catalyze the oxidation of the sulfur to $SO_3$ and reacts with sulfuric acid to give magnesium sulfate. This compound is deposited as a protective dust on the components of the combustion device and, moreover, does not pollute the environment if it is released into the atmosphere.

The development of carbon black and the formation of $SO_3$ during combustion of heating oils can, therefore, be drastically reduced by addition of oil-soluble iron and magnesium compounds. This results in an increase in the economic efficiency of the combustion of the heating oil; since the carbon content of the oil is utilized more completely, the temperature of the combustion gases can be lowered, and the sulfuric acid liberated can cause damage neither to the combustion devices nor the environment.

The iron and magnesium salts of aliphatic carboxylic acids used as additives for heating oils are prepared separately. A water-soluble iron salt, for example the nitrate, is usually employed as the starting material and is reacted with an aliphatic carboxylic acid in the presence of an alkali metal hydroxide. The magnesium salt is obtained by reaction of magnesium oxide or magnesium carbonate with the carboxylic acid at temperatures above 120° C. In spite of the high temperatures, the reaction time is at least 2 hours. The use of such high temperatures leads to caking in the reactor, which impedes uniform reaction of the magnesium oxide and carboxylic acid and thus leads to impure products and makes emptying of the reactor difficult.

DESCRIPTION OF THE INVENTION

It is thus the object of the invention to develop a procedure which enables mixtures of oil-soluble iron and magnesium salts of aliphatic carboxylic acids to be obtained in a simple manner without caking and within short reaction times.

The invention is a process for the preparation of a mixture of oil-soluble iron and magnesium salts of saturated aliphatic monocarboxylic acids. It comprises reacting magnesium oxide, at temperatures of 50° to 100° C., with a stoichiometric equivalent or excess of a saturated aliphatic monocarboxylic acid having 6 to 8 carbon atoms in a solution comprising an iron salt of a saturated aliphatic monocarboxylic acid having 6 to 8 carbon atoms in an organic solvent.

Surprisingly, the time for the reaction of the magnesium oxide with the aliphatic carboxylic acid is shortened significantly in the novel process in comparison with a process in which only magnesium oxide and the aliphatic carboxylic acid are reacted. No caking problems occur either during the reaction or during emptying of the reactor. The magnesium oxide reacts completely, so that the carboxylate is not contaminated with the starting magnesium compound employed.

The solution of an iron salt of a saturated aliphatic monocarboxylic acid having 6 to 8 carbon atoms in a suitable organic solvent is used as the reaction medium. The acid on which the salt is based can be straight or branched chain and, in particular, α-branched. Examples of such acids are 2-ethylbutyric acid, 2,3-dimethylbutyric acid, 2-methylpentanoic acid, 2-ethylpentanoic acid, 2-ethylhexanoic acid, and isooctanoic acid. 2- ethylhexanoic acid is preferred. The iron is in the form of the iron (III) ion in the salts.

Possible organic solvents are those substances or mixtures in which the carboxylates and the free monocarboxylic acid are soluble. Aliphatic or aromatic hydrocarbons or hydrocarbon mixtures, such as kerosene, toluene and xylene, and, in particular, mineral oil fractions having boiling ranges between about 150° and about 300° C., have proved suitable.

The reaction medium is prepared by simply dissolving the iron carboxylate in the organic solvent. The aqueous solution of an iron salt, for example, the nitrate, can also be used as starting substance; approximately the equivalent amount of an alkali metal salt of the monocarboxylic acid, likewise in an aqueous solution, is added thereto. The aqueous phase is then extracted with the organic solvent. It is possible to employ amounts of monocarboxylic acid and alkali metal hydroxide or carbonate equivalent to the amount of iron instead of the alkali metal carboxylate. In this case also, more or less than the equivalent amount of acid and alkali metal compound does no harm.

An amount of a $C_6$ to $C_8$ monocarboxylic acid at least equivalent to the amount of magnesium oxide to be reacted is dissolved in the iron carboxylate solution as the reaction medium. This acid can be straight or branched chain and, in particular, is $\alpha$-branched. Examples of such acids are 2-ethylbutyric acid, 2,3-dimethylbutyric acid, 2-methylpentanoic acid, 2-ethylpentanoic acid, and 2-ethylhexanoic acid, 2-ethylhexanoic acid being preferred. For best results, the excess of acid should not be more than 30%, advantageously from about 10 to 30%.

The magnesium oxide is suspended in the solution described above. The commercially available types of magnesium oxide can be used. Weakly calcined magnesium oxides, i.e. those which originate, for example, from the carbonate by splitting off $CO_2$ just above the decomposition point, are particularly suitable. The magnesium oxide is dissolved by heating the reaction mixture to temperatures between 50° and 100° C., in particular 60° to 80° C. Higher temperatures are best avoided because of the risk of caking; the lower temperatures may lead to a prolonging of the reaction times.

Other variants of the reaction between magnesium oxide and monocarboxylic acid are, of course, also possible. Thus, the magnesium oxide can be suspended in the reaction medium and the acid can be added to the reaction mixture in portions.

According to another embodiment of the process according to the invention, approximately the equivalent amount of an alkali metal carboxylate and the amount of monocarboxylic acid required for conversion of the magnesium oxide are added to the aqueous solution of an iron salt. The mixture is then extracted with the organic solvent. The aqueous phase is separated off, the magnesium oxide is added to the organic phase, and the organic phase is heated until the magnesium oxide has dissolved. It goes without saying that the alkali metal carboxylate can be replaced by the carboxylic acid and the equivalent amount of alkali metal hydroxide or carbonate.

The concentration of the iron salt in the organic solvent used as the reaction medium is not critical. It largely depends on the solubility of the iron and magnesium compound in the solvent and the further use of the solution.

The concentration of the two salts in the solvent can also be varied over wide ranges. The envisaged use of the solution and its convenience are again the deciding factors, since its flowability decreases as the salt content increases. Solutions in mineral oil fractions as solvents usually contain 5 to 8% by weight of the salts, it being the rule of thumb that the mixtures in which the iron salt predominates give solutions of higher concentration than mixtures having a larger content of the magnesium salt.

The mixtures according to the invention of oil-soluble iron and magnesium carboxylates have proved to be suitable as combustion auxiliaries for liquid fuels. Liquid fuels in the context of the present invention are understood as substances for generating heat, such as middle distillates of petroleum, for example, heating oil EL or heavy heating oil. The salt mixture is added to the liquid fuel in an amount and composition such that the iron concentration in the fuel is 5 to 100 ppm and the amount of magnesium present as a salt is sufficient to bond, as $MgSO_4$, up to 30% by weight of the sulfur contained in the fuel. Preferably, the iron concentration in the fuel should be 5 to 25 ppm and the amount of magnesium should be sufficient to bond the sulfur converted into sulfur trioxide.

The salt mixture can be added, in solid or dissolved form, to the fuel by itself or together with other additives. It has proved appropriate to use the salt mixture in the solution obtained during preparation.

The process according to the invention is described in more detail in the example which follows, without limiting it to this embodiment.

EXAMPLE

A mixture of 59.2 g of sodium hydroxide solution (32.4% strength by weight, corresponding to 0.48 mol) and 152.8 g of 2-ethylhexanoic acid (1.06 mol) is added dropwise to a solution of 64.7 g of iron nitrate in 200 ml of water at 80° C. over a period of 10 minutes. The mixture is subsequently allowed to react at 80° C. for 20 minutes, and about 150 ml of a mineral oil fraction which boils above 270° C. is added. After cooling to 40° C., the aqueous phase and the organic phase are separated. The organic solution is heated to 80° C., and 8.2 g (0.2 mol) of magnesium oxide is added; this dissolves completely within 1 hour. The solution of the two carboxylates is still slightly cloudy due to water; this is removed from the organic phase by centrifugation. The solution contains 3% by weight of iron and 1.6% by weight of magnesium and its viscosity at 20° C. is about 53 mPa.

While only a limited number of specific embodiments of the invention have been expressly disclosed it is, nonetheless, to be broadly construed and not to be limited except by the character of the claims appended hereto.

What we claim is

1. A process for the preparation of a mixture of oil-soluble iron (III) and magnesium salts of saturated aliphatic monocarboxylic acids comprising reacting magnesium oxide with at least an equivalent amount of a first saturated aliphatic monocarboxylic acid having 6 to 8 carbon atoms in a solution of an iron (III) salt of a second saturated aliphatic monocarboxylic acid having 6 to 8 carbon atoms in an organic solvent.

2. The process of claim 1 wherein said second monocarboxylic acid is $\alpha$-branched.

3. The process of claim 1 wherein said second acid is selected from the group consisting of 2-ethylbutyric acid, 2,3-dimethylbutyric acid, 2-methylpentanoic acid, 2-ethylhexanoic acid, and isooctanoic acid.

4. The process of claim 2 wherein said second monocarboxylic acid is 2-ethylhexanoic acid.

5. The process of claim 1 wherein said organic solvent is selected from the group consisting of aliphatic hydrocarbons, aromatic hydrocarbons, and mixtures thereof.

6. The process of claim 5 wherein said organic solvent is selected from the group consisting of kerosene, toluene, and xylene, and mineral oil fractions having boiling points between about 150° and 300° C.

7. The process of claim 6 wherein said organic solvent is said mineral oil fractions.

8. The process of claim 1 wherein said first monocarboxylic acid is α-branched.

9. The process of claim 1 wherein said first acid is selected from the group consisting of 2-ethylbutyric acid, 2-3-dimethylbutyric acid, 2-methylpentanoic acid, 2-ethylhexanoic acid, and isooctanoic acid.

10. The process of claim 9 wherein said first monocarboxylic acid is 2-ethylhexanoic acid.

11. The process of claim 1 wherein said MgO is weakly calcined.

12. The process of claim 11 wherein said MgO is produced by heating magnesium carbonate to its decomposition point or slightly above.

13. The process of claim 1 which is carried out at a temperature of 50° to 100° C.

14. The process of claim 13 wherein said temperatures are 60° to 80° C.

15. A process for the preparation of a mixture of iron (III) and magnesium salts of saturated aliphatic monocarboxylic acids having 6 to 8 carbon atoms comprising adding as first amount of an alkali metal aliphatic monocarboxylate and a second amount of an aliphatic saturated monocarboxylic acid to an aqueous solution of an iron (III) salt to form a mixture, extracting said mixture with an organic solvent whereby an aqueous phase and an organic phase are formed, separating said aqueous phase from said organic phase, adding magnesium oxide to said organic phase, and heating said organic phase until said magnesium oxide is dissolved, said first amount being approximately equivalent to said iron (III) salt and said second amount is that required for conversion of said magnesium oxide to said magnesium salts.

16. The method of claim 1 wherein said first acid and said second acid are the same.

* * * * *